United States Patent
Artunduaga

(10) Patent No.: US 11,000,210 B2
(45) Date of Patent: *May 11, 2021

(54) SYSTEMS, DEVICES, AND METHODS FOR PERFORMING ACTIVE AUSCULTATION AND DETECTING SONIC ENERGY MEASUREMENTS

(71) Applicant: RESPIRA LABS, INC., Mountain View, CA (US)

(72) Inventor: Maria Artunduaga, Mountain View, CA (US)

(73) Assignee: Respira Labs, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/926,399

(22) Filed: Jul. 10, 2020

(65) Prior Publication Data

US 2020/0367787 A1     Nov. 26, 2020

Related U.S. Application Data

(63) Continuation of application No. 16/542,103, filed on Aug. 15, 2019, now Pat. No. 10,709,355, which is a continuation of application No. PCT/US2019/029481, filed on Apr. 26, 2019.

(60) Provisional application No. 62/773,002, filed on Nov. 29, 2018, provisional application No. 62/663,262, filed on Apr. 27, 2018.

(51) Int. Cl.
*A61B 5/091* (2006.01)
*A61B 7/00* (2006.01)
*G10L 25/51* (2013.01)

(52) U.S. Cl.
CPC ............. *A61B 5/091* (2013.01); *A61B 7/003* (2013.01); *G10L 25/51* (2013.01)

(58) Field of Classification Search
CPC ............ A61B 5/91; A61B 7/003; G10L 25/51
See application file for complete search history.

(56) References Cited

U.S. PATENT DOCUMENTS 4,672,977 A     6/1987 Kroll
5,610,987 A     3/1997 Harley
(Continued)

OTHER PUBLICATIONS

Arjomandi M, et al., "Lung volumes identify an at-risk group in persons with prolonged secondhand tobacco smoke exposure but without overt airflow obstruction," BMJ Open Resp Res 2018;5:e000284. doi:10.1136/bmjresp-2018-000284, 11 pages.
Brusasco, Vito, et al., "Chronic Obstructive Pulmonary Disease," American Physiological Society. Compr Physiol 4:1-31, 2014.
Calligaro, Gregory L., et al., "Comparing Dynamic Hyperinflation and Associated Dyspnea Induced by Metronome-Paced Tachypnea Versus Incremental Exercise," COPD: Journal of Chronic Obstructive Pulmonary Disease, (2014) 11:1, 105-112, DOI:10.3109/15412555.2013.841669, 9 pages.
(Continued)

*Primary Examiner* — Patrick Fernandes
(74) *Attorney, Agent, or Firm* — Resonance IP Law, PC

(57) ABSTRACT

Active auscultation may be used to determine organ (e.g., lung or heart) characteristics of users. An acoustic or piezoelectric signal (e.g., a pulse, a tone, and/or a broadband pulse) may be projected into an animal (typically human) body or thorax. The signal interacts with the body, or lungs, and in some cases may induce resonance within the body/lungs. A resultant signal may be emitted from the body which may be analyzed to determine, for example, a lung's resonant frequency or frequencies and/or how the sound is otherwise absorbed, reflected, or modified by the body. This information may be indicative of lung characteristics such as lung capacity, a volume of air trapped in the lungs, and/or the presence of COPD.

25 Claims, 14 Drawing Sheets

(56) References Cited

U.S. PATENT DOCUMENTS

| | | |
|---|---|---|
| 6,443,907 B1 | 9/2002 | Mansy et al. |
| 6,790,183 B2 | 9/2004 | Murphy |
| 7,165,451 B1 | 1/2007 | Brooks et al. |
| 7,347,824 B2 | 3/2008 | Wilkinson et al. |
| 8,221,323 B2 | 7/2012 | Zhang et al. |
| 8,517,016 B2 | 8/2013 | Caro et al. |
| 9,078,571 B2 | 7/2015 | Bridger et al. |
| 9,795,358 B2 | 10/2017 | Telfort et al. |
| 9,900,677 B2 | 2/2018 | Hung et al. |
| 2004/0037429 A1 | 2/2004 | Candioty |
| 2004/0260188 A1 | 12/2004 | Syed et al. |
| 2006/0100666 A1 | 5/2006 | Wilkinson et al. |
| 2007/0055175 A1 | 3/2007 | Caro |
| 2008/0039733 A1 | 2/2008 | Unver et al. |
| 2009/0036777 A1* | 2/2009 | Zhang .................. A61B 5/4878 600/459 |
| 2009/0171231 A1* | 7/2009 | Caro ...................... A61B 7/003 600/529 |
| 2016/0287140 A1 | 10/2016 | Beyar et al. |
| 2020/0000371 A1 | 1/2020 | Artunduaga |

OTHER PUBLICATIONS

Gagnon, Philippe, et al., "Pathogenesis of hyperinflation in chronic obstructive pulmonary disease," Int J Chron Obs Pulm Dis, 9 (2014), pp. 187-201.

International Search Report and Written Opinion of the International Searching Authority issued in PCT/US2019/029481 dated Jul. 16, 2019.

Lahaije, A. et al., "Can COPD Patients Who Hyperinflate During Daily Life Activities Be Identified by Laboratory Tests?" Respiration 2013;86:237-242.

Zafar, Muhammad Ahsan et al., "Dynamic Hyperinflation Correlates with Exertional Oxygen Desaturation in Patients with Chronic Obstructive Pulmonary Disease," Lung (2013) 191:177-182.

Zeng, Siyang, et al., "Lung Volume Indices Predict Morbidity in Smokers wth Preserved Spirometry," Thorax. Feb. 2019;74(2):114-124. doi: 10.1136/thoraxjnl-2018-211881. Epub Jul. 20, 2018.

* cited by examiner

US 11,000,210 B2

SYSTEMS, DEVICES, AND METHODS FOR PERFORMING ACTIVE AUSCULTATION AND DETECTING SONIC ENERGY MEASUREMENTS

RELATED APPLICATIONS

This application is a CONTINUATION of U.S. patent application Ser. No. 16/542,103, entitled "SYSTEMS, DEVICES, AND METHODS FOR PERFORMING ACTIVE AUSCULTATION AND DETECTING SONIC ENERGY MEASUREMENTS" filed Aug. 15, 2019, which is a NATIONAL PHASE APPLICATION of PCT/US2019/029481, entitled "SYSTEMS, DEVICES, AND METHODS FOR PERFORMING ACTIVE AUSCULTATION AND DETECTING SONIC ENERGY MEASUREMENTS" filed Apr. 26, 2018, which is a NON-PROVISIONAL of, and claims priority to, U.S. Provisional Patent Application No. 62/663,262 entitled "ACTIVE AUSCULTATION DEVICE AND SONIC ENERGY MEASUREMENT SENSOR" filed Apr. 27, 2018, and is a NON-PROVISIONAL of, and claims priority to, U.S. Provisional Patent Application No. 62/62/773,002 entitled "SYSTEMS, DEVICES, AND METHODS FOR PERFORMING ACTIVE AUSCULTATION AND SONIC ENERGY MEASUREMENTS" filed Nov. 29, 2018 both of which are incorporated by reference, in their entireties, herein.

BACKGROUND

Auscultation is used to determine conditions of organs within an animal body, typically the heart or lungs. A signal is introduced into the body often times by manually tapping the chest or back. After that signal has interacted with the organ of interest (typically the lungs), it is detected by a stethoscope. By analyzing the detected signal, conditions of the organ can be determined.

BRIEF DESCRIPTION OF THE DRAWINGS

The present invention is illustrated by way of example, and not limitation, in the figures of the accompanying drawings in which.

Figure 1:
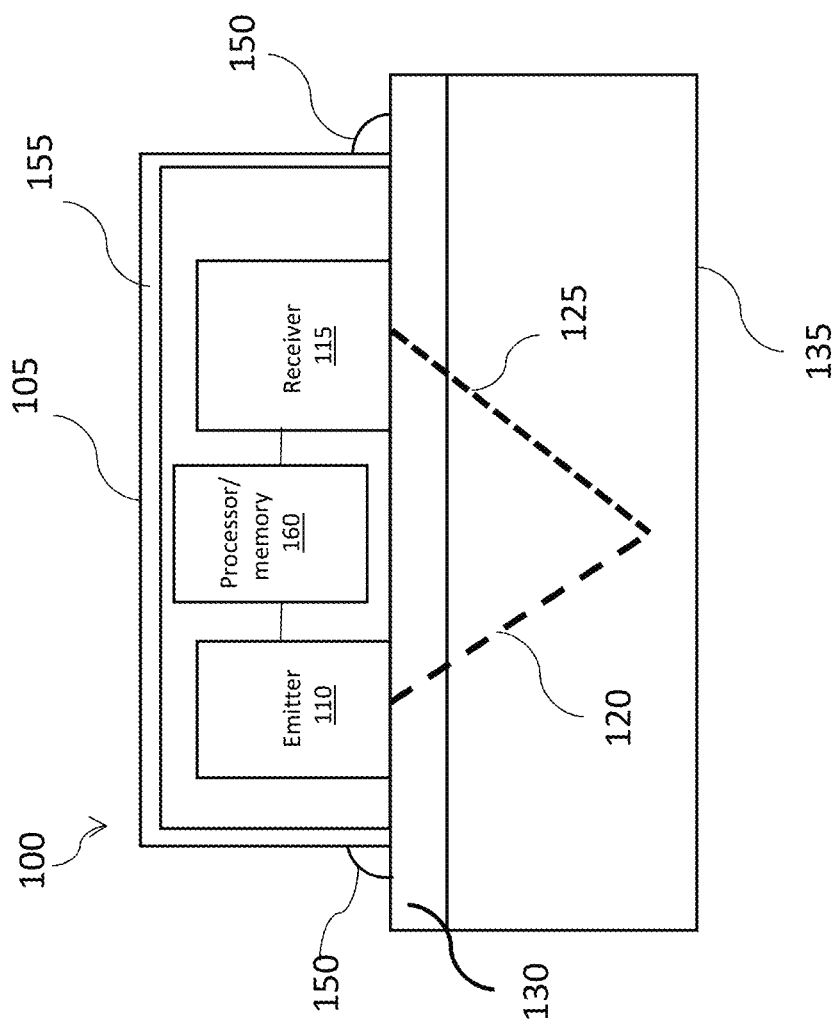
FIG. 1 shows an exemplary active auscultation system, consistent with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

SUMMARY

The present invention active auscultation to determine organ (e.g., lung or heart) characteristics of users. An acoustic or piezo-electric signal (e.g., a pulse, a tone, and/or a broadband pulse) is projected into an animal (typically human) body or chest. The signal interacts with the body, or lungs, and in some cases may induce resonance within the body/lungs. A resultant signal may be emitted from the body which may be analyzed to determine, for example, a lung's resonant frequency or frequencies and/or how the sound is otherwise absorbed, reflected, or modified by the body. This information may be indicative of lung characteristics such as lung capacity and/or the presence of COPD.

One method of active auscultation disclosed herein projects an acoustic signal into user's body toward a target of interest, often times, the user's heart and/or lung(s). The acoustic signal may be projected into the user's body continuously, periodically, and or as pulse or short-duration burst that may last for approximately 0.1-5 seconds. In some embodiments, the acoustic signal may be a broadband signal including a plurality of frequencies ranging from, for example, 2,000 Hz and 30,000 Hz.

A portion of the acoustic signal may emanate from the user's body via, for example, back scattering or transmission and may be received by a receiver such as a microphone. A characteristic of the received acoustic signal may then be determined. Exemplary characteristics include an intensity, a duration, and/or a frequency of the received acoustic signal. The characteristic may be provided to an operator.

In some embodiments, these steps may be repeated a plurality of times and characteristics of the received sound may be compared with one another to determine, for example, changes in the characteristic over time and/or whether a determined characteristic corresponds with another factor such as an improvement to the user's health, an adverse health event, a weather factor, an environmental factor, etc. The comparison may be provided to an operator.

Additionally, or alternatively, the determined characteristic may be compared to a predetermined value for the characteristic in order to determine, for example, how the user's characteristic compares with other characteristics in order to deduce a similarity or pattern which may be used to diagnose the user and/or predict when an adverse event is likely to occur.

Additionally, or alternatively, in some instances, a duration, an intensity, and/or frequencies included in the signal may be adjusted responsively to, for example, the determined characteristics of the received acoustic signal and/or a lack of a sufficiently clear received acoustic signal.

In some instances, the characteristic may be used to determine a volume of air trapped in the user's lung and/or a lung capacity for the user.

Additionally, or alternatively, in some embodiments, active auscultation may be performed by providing, by a processor in communication with an emitter, signal stimuli to the emitter so that the emitter produces acoustic energy of a plurality of frequencies, the acoustic energy being directed towards an organ of a user. An acoustic energy response that corresponds to the acoustic energy of the plurality of frequencies directed towards to the organ may then be received and analyzed to determine a resonant frequency for the organ. In some embodiments, the plurality of frequencies directed towards the organ may include a set of discrete frequencies, a predetermined frequency response, and/or a bin of frequencies. Additionally, or alternatively, the signal stimuli may cause the emitter to produce acoustic energy that cycles through the set of discrete frequencies over a predetermined period of time. Additionally, or alternatively, the signal stimuli may cause the emitter to produce acoustic energy that includes a series of pseudo-randomly generated and/or selected frequencies. Additionally, or alternatively, the signal stimuli may cause the emitter to produce acoustic energy to produce a burst of acoustic energy that includes the plurality of frequencies.

In some embodiments, a volume of air trapped in the organ may be determined based on the resonant frequency for the target.

In some embodiments disclosed herein, information pertaining to the user may be received and correlated to the resonant frequency of the target and/or organ. At times, the received information pertains to one or more of a physiological characteristic of a user, a diagnosis of a user, a size of the organ, a shape of the organ, a type of fluid in the organ, a type of gas in the organ, a location of the emitter, a location of the receiver, a level of ambient noise, and an orientation of a user.

Exemplary systems disclosed herein may include a processor and/or server configured to provide signal stimuli to an emitter (e.g., a speaker) in communication with the processor such that the emitter produces acoustic energy of a plurality of frequencies. The acoustic energy may be directed towards an organ of a user's body. An acoustic energy response that corresponds to the acoustic energy of the plurality of frequencies directed towards to the organ may be received by the processor/server and the processor/server may generate a comparison between the acoustic energy response and a predetermined threshold and then determine, based on the comparison, one or more resonant frequencies for the organ.

Additionally, or alternatively, active auscultation may be performed by providing, by a processor in communication with an emitter, a first signal stimuli to the emitter such that the emitter produces acoustic energy of a first plurality of frequencies that is directed towards an organ, receiving, by the processor, via a receiver in communication with the processor, a first acoustic energy response that corresponds to the acoustic energy of the first plurality of frequencies directed towards the organ, providing, by the processor, a second signal stimuli to the emitter such that the emitter produces acoustic energy of a second plurality of frequencies that is directed towards the organ, receiving, by the processor, via the receiver, a second acoustic energy response that corresponds to the acoustic energy of the second plurality of frequencies directed towards the organ, generating, by the processor, a comparison between the first acoustic energy response and the second acoustic energy response, and determining, by the processor, based on the generated comparison, one or more characteristics of the organ.

In some embodiments, a wearable auscultation sensor used herein may include an emitter configured to project an acoustic signal into a user's body, a receiver configured to receive an acoustic signal emanating from the user's body, and a noise cancelling device configured reduce ambient noise in the received acoustic signal. The noise cancelling device may be mechanical and/or electronic/acoustic in nature. In some instances, the noise cancelling device may include noise-cancelling circuitry specifically designed to cancel unwanted ambient noise of known and/or unknown frequencies. In some embodiments, the noise cancelling device may analyze the ambient noise and add a signal to the received signal that is 180 degrees out of phase with the ambient noise to filter the ambient noise from the received signal.

WRITTEN DESCRIPTION

A system (e.g. a physical object) that amplifies sound waves on frequencies that match one or more of the system's natural vibration frequencies is a definition of acoustic resonance. Once the object is excited with energy at frequencies unrelated to their natural vibration frequencies, the energy will quickly dissipate. But when the excitation approximates one of the object's natural vibration frequencies, the object will start to resonate and vibrate strongly in this frequency. An object's resonant frequencies may be found by exciting it with, for example, a specific frequency, a set of frequencies, a broadband signal (e.g. noise composed of many frequencies), a pseudo-randomly generated frequency or range of frequencies, a chirp signal, and/or a white noise signal.

Systems, devices, and methods for performing active auscultation and sonic energy measurements that utilize resonance are herein described. The systems, devices, and methods may use an active acoustic sensor, digital signal processing, and machine learning for continuous, long-term and non-invasive lung-health monitoring. Exemplary systems and devices include a sound or acoustic energy transducer/emitter (e.g., a speaker) and a sonic energy transducer/receiver (e.g., a microphone). Often times, the emitter may be configured to emit sound within a range (e.g., 20 Hz to 100 kHz) that will pass through a user's skin and penetrate a portion of his or her body (e.g., thorax or chest) and the receiver may be configured receive sound within this range.

Lung function assessment and COPD diagnosis and monitoring are often done using a variety of functional tests (e.g., spirometry, plethysmography), imaging techniques (e.g., CAT Scan, X-rays), and doctor observation and examination. These techniques require specialized equipment and often must take place in a medical environment and be administered by medical professionals. Spirometry and other tests require the user to stop all activity and breathe on a device in a certain way. This makes continuous lung function monitoring cumbersome, a substantial disruption to a user's daily routine, and difficult for home care.

The systems, devices, and methods disclosed herein may be used to measure acoustic resonance in a user's body or portions thereof (e.g., organs such as the lungs or heart). Characteristics of measured resonance may be affected by, for example, air, liquid, or fat included within the user's body or target tissue and/or other physiological properties that may be responsive to acoustic stimuli.

In one embodiment, the measured resonance may be used to detect and/or determine a severity of air trapped in a user's lungs. Air may be trapped in a user's lungs as a result of a respiratory condition of the user (e.g., Chronic Obstructive Pulmonary Disease (COPD or asthma). Additionally, or alternatively, measured characteristics of resonance may be used to monitoring the air changes on lungs during the respiratory cycle (i.e., inhalation and exhalation) and may be used to compare one region of the body with another (e.g., compare one lung with another lung).

In some embodiments, the present invention may be used to track lung function over time in order to, for example, establish a baseline of lung function and monitor changes from the baseline as a way of monitoring lung health. This may be helpful when deciding whether or not a user may be susceptible to an infection or adverse event (e.g., an asthma attack) so that preventative measures may be taken and/or treatments administered.

The emitter and receiver may be housed in the same or independent housings. The housing may assist with the projection of acoustic energy into a target location within a user's body by the emitter and/or reception of sound exiting the user's body by the receiver. For example, a shape or feature of a housing may direct acoustic energy toward a target and/or assist with the detection of sound emanating from the user's body.

The housing may be configured to be positioned adjacent to the user's skin. This positioning may reduce noise (e.g., ambient noise, cross-talk, etc.) introduced into the signal received by the receiver because, for example, noise may not be able to enter the receiver via a gap, or space, between the housing and the user's skin. Additionally, or alternatively, an exemplary housing may include one or more mechanical and/or electronic noise-reducing mechanisms to prevent ambient sound from being detected by the receiver.

In some embodiments, a housing may include a plurality of emitters and/or receivers. Additionally, or alternatively, a system may include a plurality of emitters and/or receivers each within their own housing that may be configured to, for example, be placed at various locations on a user.

The systems, devices, and methods disclosed herein have the potential to standardize part of the auscultation routine by eliminating the need for users to generate sound by, for example, coughing, sneezing, or breathing to generate the sounds in the lungs that are received.

Turning now to the figures, FIG. 1 shows an exemplary active auscultation system 100 that includes an exemplary housing 105 for an emitter 110, a receiver 115, a processor/memory 160 communicatively coupled to the emitter 110 and receiver 115, and an optional mechanical noise reduction mechanism 150. In some instances, active auscultation system 100 may also include a transceiver by which it may communicate with an external electronic device (e.g., a computer or smart phone) (not shown) via, for example, a wireless communication protocol. Emitter 110 may be any device that emits and/or is capable of producing a sound, vibration, wave, and/or pulse. Exemplary emitters 110 include, but are not limited to, speakers, shakers, piezoelectric transducers, electromechanical transducers, or any other device capable of converting electrical signals into audio waveforms by, for example, exciting the surrounding air and/or a surrounding media (e.g., skin, water, and/or subcutaneous fat).

Emitter 110 and/or receiver 115 may be positioned within housing 105 so that it/they may be proximately positioned to the surface of a user's skin 130 as shown in FIG. 1. In some instances, emitter 110 and/or housing 105, may be positioned on a user's body so that sound may be delivered to the skin layer 130 and directed to a target within the body 135 such as, but not limited to, an organ like the lung or heart. Often times, housing 110 will be positioned on the thorax of the user to facilitate communication of acoustic energy to the chest cavity.

In some embodiments, housing 105 may be configured to allow for movement across the user via, for example, sliding along a strap or manually moved by an operator (e.g., a physician) to analyze the acoustic energy reflected and/or emitted by the user. Mechanical noise reduction mechanism 150 may be any material configured to mechanically prevent ambient noise from reaching receiver 115 including foam, fibers, or other materials that absorb sound. In some embodiments, mechanical noise reduction mechanism 150 surrounds a perimeter of housing 105 and may be positioned such that it is coincident with user's skin 130. Although not shown in FIG. 1, in some embodiments, mechanical noise reduction mechanism 150 may extend over and cover a portion, or all of housing 105. Additionally, alternatively, mechanical noise reduction mechanism 150 may extend under housing 105 (not shown) so as to form a noise-reducing interface between housing 105 and user's skin 130. Additionally, alternatively, mechanical noise reduction mechanism 150 may be resident within housing 105 (not shown) as, for example, a noise-reducing foam or fiber that occupies space within housing not otherwise occupied by components of active auscultation system 100. Additionally, or alternatively, a mechanical noise reduction mechanism may be a lining 155 positioned on the inside and/or outside of housing 105.

Processor/memory 160 may be configured to execute one or more instructions which may be stored in the memory. For example, processor/memory 160 may provide emitter 110 with signal stimuli that causes the emitter to produce acoustic energy of one or more frequencies (also referred to herein as a source signal). This source signal is represented in FIG. 1 as a first dashed line 120, which passes through skin layer 130 into target region of the body 135. In some instances, emitter 110 may be provided with a broadband signal stimuli or other signal that exploits multiple frequencies so that the source signal is of multiple frequencies. This source signal may provide these multiple frequencies simultaneously (i.e., the source signal includes multiple frequencies at once) and/or the source signal may include a succession of multiple frequencies, each projected by the emitter at a different time. Processor/memory may also store and/or cache received signals for later transmission to, for example, a communication device like communication device 310 as will be discussed below with regard to FIGS. 3A-3C.

In some embodiments, processor/memory 160 may adjust the signal stimuli based on one or more factors that may include, but are not limited to, physiological factors of the user (e.g., gender, body mass index, age, etc.), a diagnosis of the user, a size and/or shape of a target, a type of fluid or gas that may be present within the body or target 135, a location of the sensors, a level of ambient noise, an orientation of the user (e.g., vertical or horizontal), and so on.

In some instances, the stimuli may coincide with, or may otherwise be similar to one or more naturally occurring frequencies of target (e.g., organ of interest) that may be caused by, for example, rhythmical movement (e.g., breathing or heartbeat) and/or frequencies occurring within the ambient environment (e.g., fan noise, equipment noise). In these embodiments, the stimuli may be adjusted so that the target's response to the stimuli may be more easily discernable from these frequencies.

In some embodiments, emitter(s) 110 may generate mutually orthogonal signals (e.g. pseudorandom noise with different keys) simultaneously. When received, these mutually orthogonal signals may then be used to decorrelate an intensity of the return signal of different frequencies. Additionally, or alternatively, source signals may be emitted using time division across a plurality of emitters 110 positioned at a plurality of locations on the user.

The receiver then receives an acoustic energy signal that is emanating from the user's body via, for example, reflection, or resonance. The received acoustic energy signal is represented in FIG. 1 as a second dashed line 125. This received acoustic energy 125 (also referred to herein as a return signal) may be received by processor/memory 160, which may determine, for example, characteristics of the sound frequency and/or intensity over time. Exemplary characteristics include intensity levels per frequency, changes on overall intensity of a frequency or range of frequencies over time, and/or changes on intensity distribution for a range of frequencies over time.

On some occasions, a source signal may include a plurality of frequencies, which may be referred to herein as a broadband signal and/or a white noise signal. In some cases, the frequencies included in the plurality of frequencies and/or white noise may be pseudo-randomly selected. For example, the signal stimuli may cause emitter 110 to deliver a broadband or white noise source signal that may be configured to provide a return signal that, on average, may have a flat and/or known frequency response in some, or all frequency bins. A frequency bin is a subset of frequency ranges within the range of frequencies of the source signal. For example, if the source signal provides frequencies within the range of 1-100 kHz then a frequency bin may be set range within that frequency range at a given increment (e.g., 5, 10, 15, 20, kHz etc.).

In some embodiments, the use of a white noise in/as a source signal and/or use of different types of white noise (e.g., white noise with different frequency range characteristics) may assist with the estimation of characteristics (e.g., intensity, travel time, scattering, etc.) of the return signal. In addition, for embodiments where two emitters are used (typically each emitter is placed in a different locations such as on the left and right of a user's chest so that sound may be projected into each lung of the user), each emitter may use a white noise signal with a different set of frequencies (that may be randomly or pseudo-randomly selected) so that a first white noise signal may be differentiated from another white noise when detected and/or received by one or more receivers like receiver 115. At times, analysis of the detected signals may yield information regarding cross talk or source signal leaking from one location to another.

Additionally, or alternatively, a source signal may be set to cycle through a set of frequencies by, for example, increasing and/or decreasing the frequency of a source signal over time in a periodic way (e.g., in a sinusoidal fashion) and/or a source signal may be a set of frequencies that rises or falls in, for example, a periodic, random, pseudo-random, or patterned way. This type of source signal may be referred to as a chirp signal. The user's and/or target's 135 frequency response to this chirp signal may be estimated by measuring the response signal and integrating this signal over time.

Additionally, or alternatively, a source signal may be generated using a pseudo-randomly generated frequency or range of frequencies. This may be a targeted, or narrow, range of frequencies or a broadband range of frequencies. Chirp source signals may enable accurate measurement of resonant responses of the chest and/or lungs of a user. In some instances, a plurality of chirp source signals may be used to perform multiple measurements of the user in order to, for example, determine average minimum and/or maximum amplitude and/or intensity values for the user's response to the chirp source signal.

Additionally, or alternatively, a source signal may be a brief but powerful/intense burst of acoustic energy. The return signal may then be analyzed to determine a frequency response to the burst-like source signal. An advantage to using pulses is that they may be quickly measured.

In general, acoustic pulses (i.e., source signals of brief duration) may be useful to measure not only the user's and/or target's frequency response but also determine a time-to-target (echo) for the purpose of location or positioning of active auscultation system 100 and/or a component thereof. Additionally, or alternatively, acoustic pulses may assist with identification and characterization of the crosstalk, or leaking, between multiple speakers/microphones sensors positioned on the user.

Figure 2A:
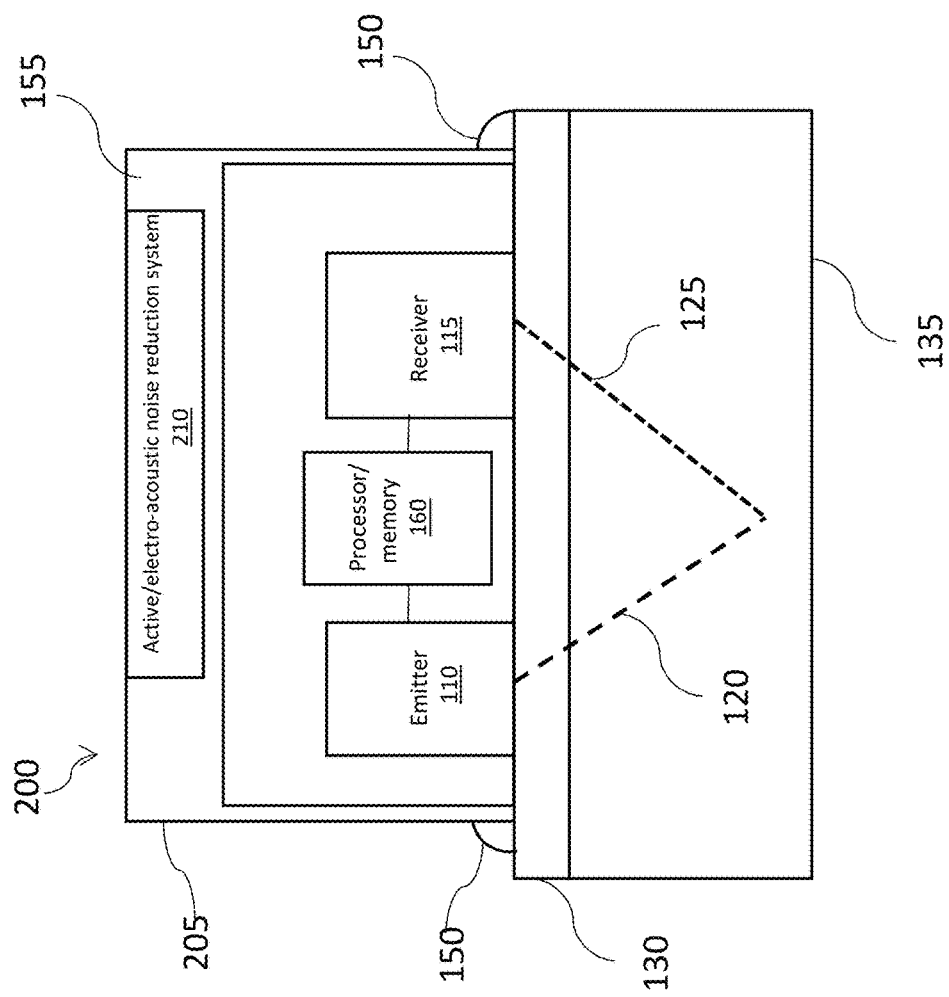
FIG. 2A illustrates a second exemplary active auscultation system, consistent with some embodiments of the present invention.

FIG. 2A illustrates a second exemplary active auscultation system 200 in communication with the user's skin 130 that includes an active, or electro-acoustic, noise reduction system. Second exemplary active auscultation system 200 includes a housing 205 that houses emitter 110, receiver 115, processor/memory 160, an optional mechanical noise reduction mechanism 150, an optional liner 155, and an active/electro-acoustic noise reduction system 210. Active/electro-acoustic noise reduction system 210 may be, for example, a receiver directed away from the user and/or emitter 110 and may be configured to capture ambient noise and/or environmental sound. Sound received active/electro-acoustic noise reduction system 210 may be used to, for example, filter received acoustic signal 125 to remove sound not emanating from the user and/or target 135 that may be considered noise. Mechanical noise reduction mechanism 150 may be implemented with housing 205 in a manner similar to its implementation with housing 105.

Figure 2B:
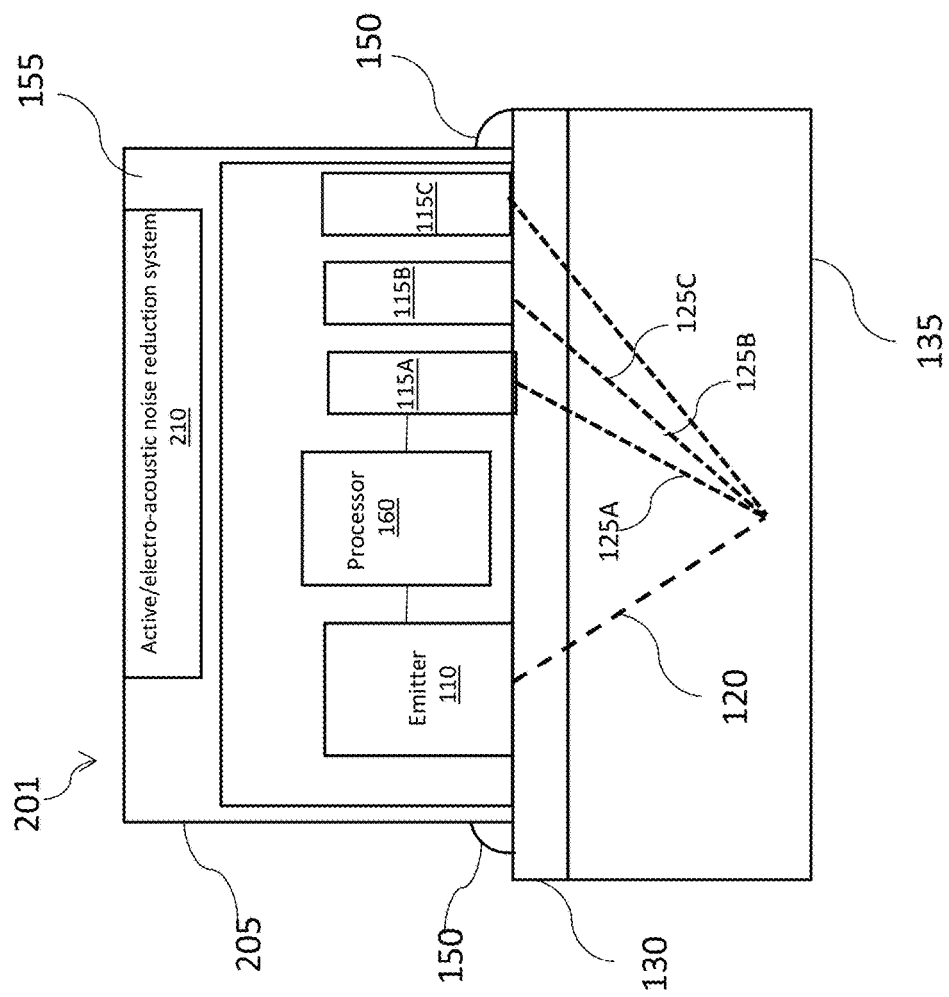
FIG. 2B illustrates a third exemplary active auscultation system, consistent with some embodiments of the present invention.

FIG. 2B illustrates a third exemplary active auscultation system 201 in communication with the user's skin that includes a plurality of receivers and an optional active, or electro-acoustic, noise reduction system. Third exemplary active auscultation system 201 includes a housing 205 that houses emitter 110, processor/memory 160, an optional mechanical noise reduction mechanism 150, an optional liner 155, an optional active/electro-acoustic noise reduction system 210, and a plurality of receivers 115A, 115B, and 115C. The plurality of receivers 115A, 115B, and 115C may be arranged in an array and may be configured to receive acoustic energy signals 125A, 125B, and/or 125C, respectively. Digital processing by, for example, processor/memory 160 and/or a processor/computer not resident within housing, such as communication device 310 and/or server 420 as discussed below with regard to FIGS. 3A-3C and FIG. 4, of received acoustic energy signals 125A, 125B, and/or 125C may serve to focus the received sound by, for example, beam forming and/or eliminating portions of the signal received from an undesirable direction (e.g., not a target location in the user's body) and/or focusing on portions of received acoustic energy signals 125A, 125B, and/or 125C coming from a point of interest.

Figure 3A:
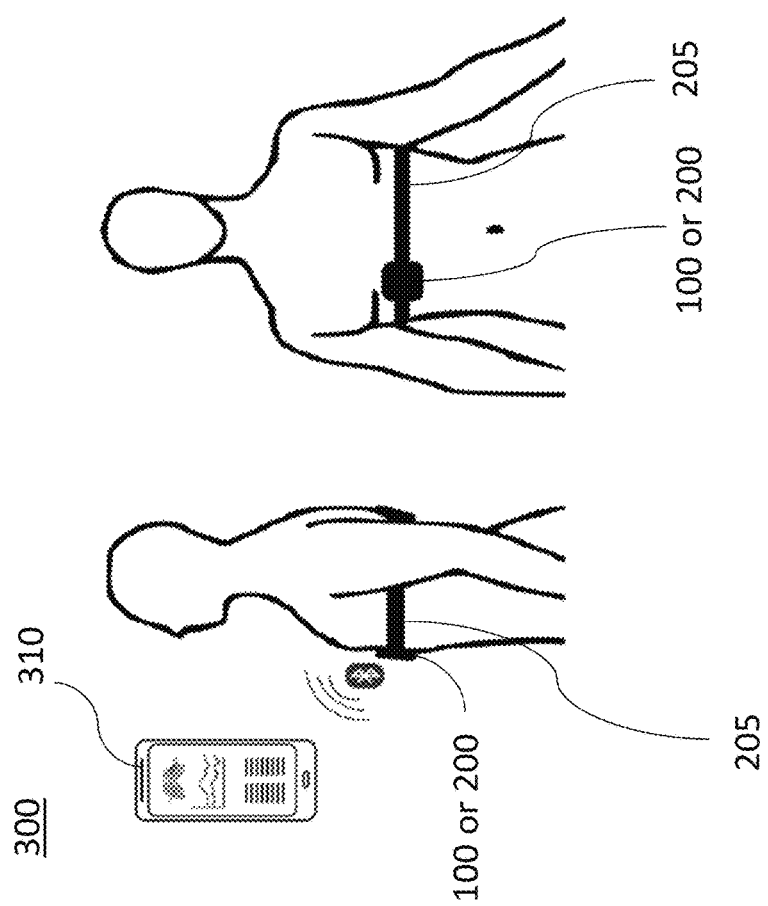
FIG. 3A provides a front and a side view of a user wearing an active auscultation system, consistent with some embodiments of the present invention.

FIG. 3A provides a front and a side view of a user wearing active auscultation system 100, 200, or 201. Active auscultation system 100, 200, or 201 is attached to the user via a mounting device (e.g., a strap or band) 205 that wraps around the user's torso and maintains a position of active auscultation system 100, 200, or 201 that is typically flush against the user's skin. Mounting device 205 may be configured to maintain a position of active auscultation system 100, 200, or 201 over time as the user wears active auscultation system 100, 200, or 201. FIG. 3A also shows an external communication device 310 in communication with active auscultation system 100, 200, or 201 via the BLUETOOTH™ wireless communication protocol. Communication device 310 may receive and/or transmit signals to active auscultation system 100, 200, or 201 and may process those signals according to one or more methods disclose herein.

Figure 3B:
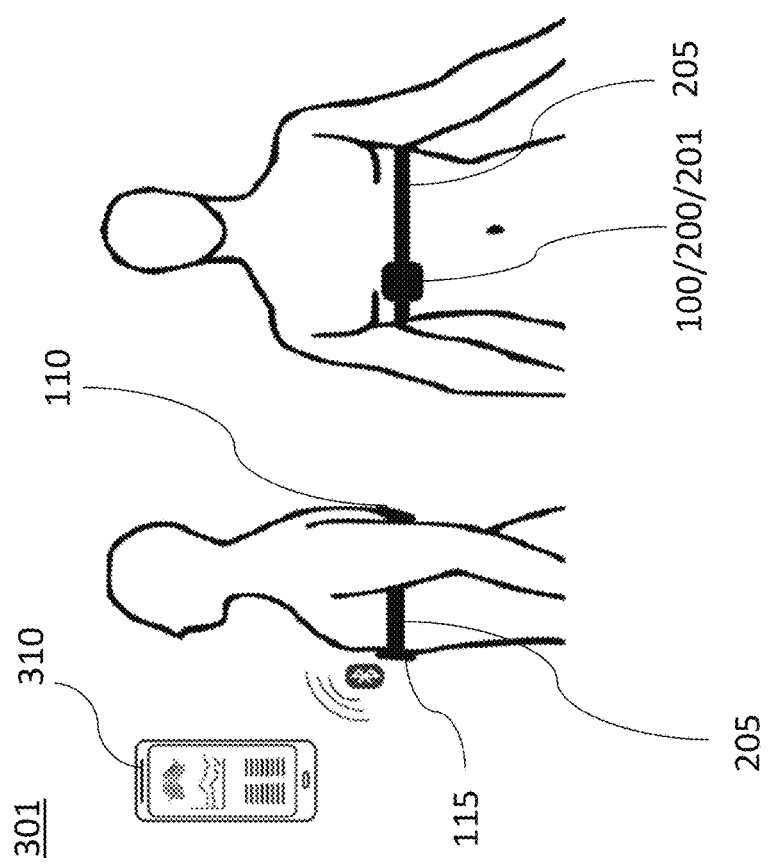
FIG. 3B provides a front and a side view of a user wearing an emitter and a receiver positioned on opposite sides of the user's thorax, consistent with some embodiments of the present invention.

FIG. 3B provides a front and a side view of a user wearing an emitter 110 and a receiver 115 positioned on opposite sides of the user's thorax. Receiver 115 and/or emitter 110 may be in communication with communication device 310 and, in some instances, their respective activity may be controlled and monitored by communication device 310.

Figure 3C:
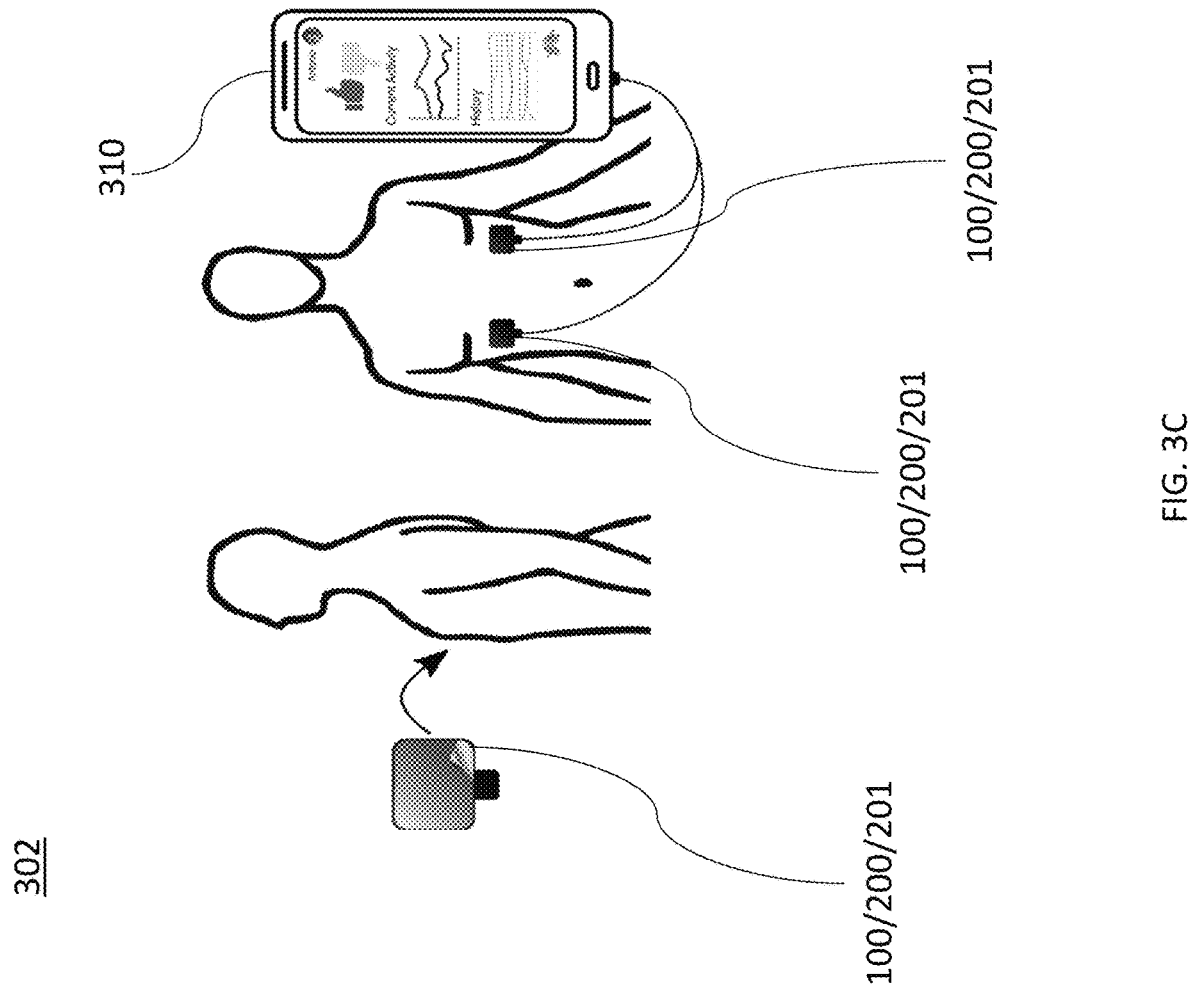
FIG. 3C provides an illustration of an exemplary active auscultation system configured as a stick-on patch that may be attached to a user's epidermis, consistent with some embodiments of the present invention.

FIG. 3C provides an illustration of an exemplary active auscultation system 100, 200, and/or 201 configured as a stick-on patch that may be attached to a user's epidermis. FIG. 3C also provides a side view of the user showing where the active auscultation system 100, 200, and/or 201 embodied as a stick-on patch may be affixed to the user's thorax. FIG. 3C further shows a front view of the user with two active auscultation systems 100, 200, and/or 201 positioned on the left and right sides of the user's thorax. Active auscultation systems 100, 200, and/or 201 may be in wired and/or wireless communication with communication device 310 and, in some instances, their respective activity may be controlled and monitored by communication device 310.

The housings, emitters, receivers, and/or systems disclosed herein may be configured for a one-time use (e.g., may be disposable) or multiple uses.

Figure 4:
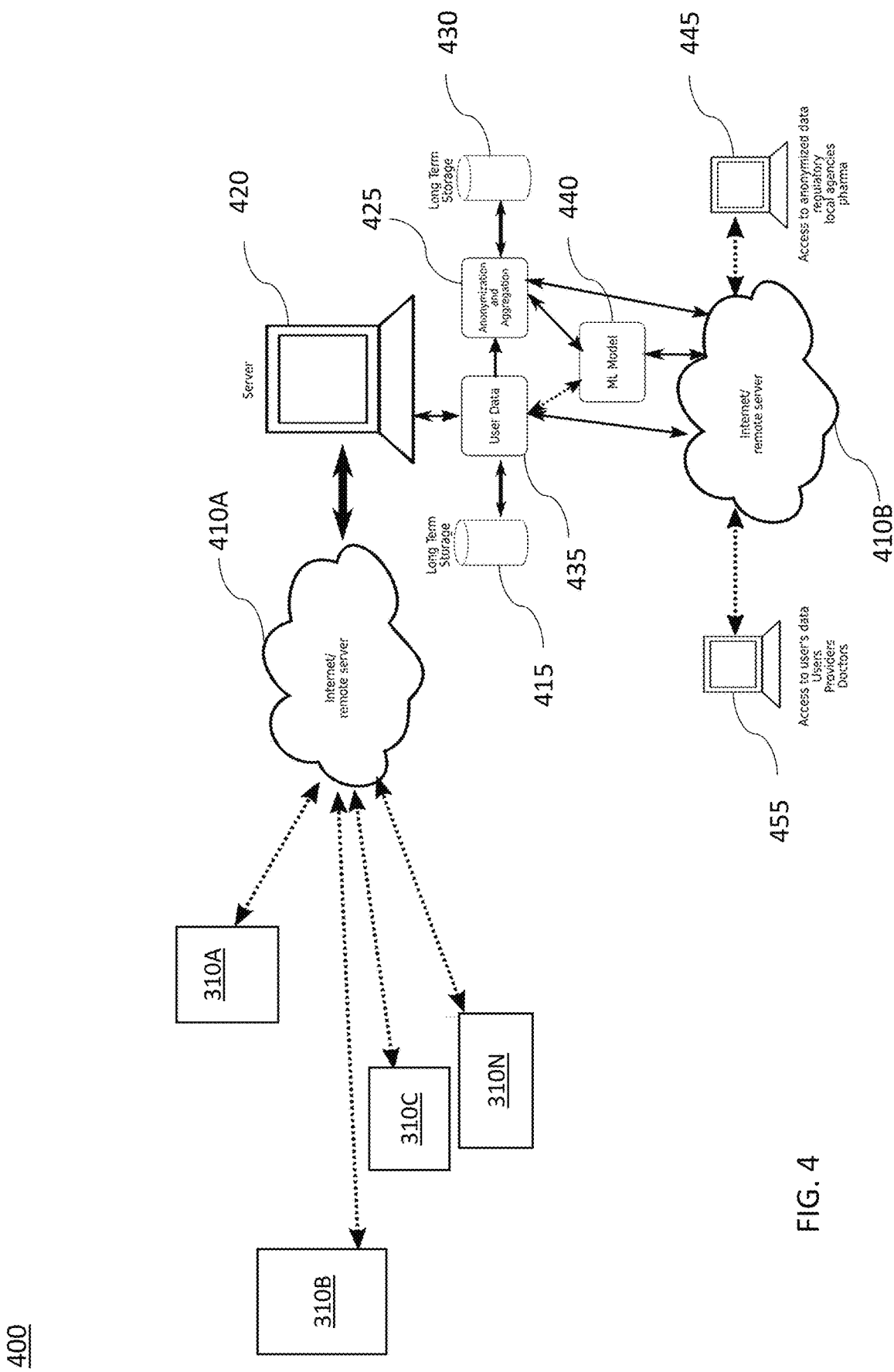
FIG. 4 provides a block diagram of a system for the acquisition and processing of active auscultation data from a plurality of communication devices, consistent with some embodiments of the present invention.

FIG. 4 provides a block diagram of a system 400 for the acquisition and processing of active auscultation data from a plurality of communication devices 310, each of which are in communication with one or more active auscultation systems 100, 200, and/or 201. System 400 may include a plurality (e.g., 100, 1000, 1,000,000, etc.) communication devices which are depicted as communication devices 310A, 310B, 310C, 310N in FIG. 4. Communication devices 310A, 310B, 310C, 310N are communicatively coupled to a server 420 via a communication network (e.g., the Internet) and/or remote server 410A. Server 420 is communicatively coupled to a first database 415 and a second database 430. Optionally, system 400 may include a private access terminal 455 and/or a public access terminal 445 either or both of which may be communicatively coupled to server for 20 database 415, and/or database 430 via a communication network e.g., the Internet) and/or remote server 410B. In some embodiments, communication network/remote server 410A and communication network/remote server 410B may be the same and/or may be communicatively coupled to one another. Components of system 400 may be communicatively coupled to one another via wired and/or wireless communication links.

Communication devices 310A-310N may receive raw and/or processed data (e.g., data from which noise has been removed, data from which one or more features have been extracted, etc.) from one or more active auscultation systems, such as, active auscultation 100, 200, and/or 201 that are being/have been worn by one of a plurality of respective users. The data may be received in real time and/or may have been cached on the respective active auscultation system until it was within communication range with a communication device 310. In some embodiments, each of the communication devices 310A-310N may add personally identifying information and/or an anonymized identifier (e.g., a string of numbers or letters used to anonymously identify the user) to the data it communicates to server 420 so that the received data may be associated with the user and/or the user's anonymous identity.

In some embodiments, one or more communication device(s) 310 may store data thereon for a short and/or long-term duration for the purpose of, for example, providing feedback and/or measurements to a user of the respective communication device 310. Additionally, or alternatively, one or more communication device(s) 310 may analyze and/or process the raw data prior to communication to server 420 by, for example, application of filters, noise reduction techniques, amplification techniques, etc. to the raw data.

Additionally, or alternatively, one or more communication device(s) 310 may the flag, or otherwise associate an indicator, with data of particular interest to, for example, the user, that user's healthcare provider, and/or a researcher. Data that may be of particular interest includes data received that correlates in time to an adverse event (e.g., a coughing fit, an onset of infection, a hospitalization, etc.) and/or an event of interest (e.g., when the user is at rest, when the user is exercising, etc.).

Additionally, or alternatively, data entered by a user and/or other ancillary data may be provided to server 420 by one or more communication devices 310A-310N. User-entered and/or ancillary data includes, but is not limited to, the user's heart rate, the user's body temperature, demographic information for the user (e.g., race, gender, age, etc.), an activity (e.g., light exercise, strenuous exercise, rest) engaged in by the user at the time of the data collection, medical diagnostic information, and medical history information. This data may be entered by the user and/or a caregiver of the user via, for example, a user interface like keyboard and/or speech-to-text recognition. The ancillary data may, in some instances, be tagged and/or time stamped to correlate with the received acoustic signals.

Server 420 may receive data (e.g., raw, processed, and/or ancillary) from the plurality of communication devices 310 and made prepare user data 435 for storage in database 415. User data 435 may include, but is not limited to, the received raw and/or processed acoustic signals and ancillary data for the user and/or correlations between the ancillary data and the received raw and/or processed acoustic signals which may be indexed and/or placed in a lookup table buy server 420 that is stored in database 420.

In some embodiments, the user data 435 may be made anonymous and/or aggregated 425 and stored in database 430. The process of making user data 435 may be consistent with any requirements for data privacy implemented by a regulatory agency, a user, and/or a health care facility or administrator.

The user data 435 and/or anomized/aggregated data 425 may be used to develop a model 440 that correlates data derived using active auscultation systems 100, 200, and/or 201 (e.g., lung resonance data and/or received acoustic signals) with ancillary and other data such as medical test data, imaging data (e.g., CT scan data, MRI scan data), medical history, geographic data, levels of pollution corresponding to a geographic location, weather, temperature, humidity, activity measured by sensors (e.g., accelerometers), and/or ad lib data entered by a user via text, email, voice commands, etc. In some instances, the models may be developed for a single user so as to, for example, monitor that user's health and/or predict changes in the user's health and/or adverse events for the user. Additionally, or alternatively, models may be developed for groups of users that share a common characteristic (e.g., level of disease progression, age, rate of oxygen consumption, geographic location, altitude, disease stage, occupation, etc.). Additionally, or alternatively, models may be developed for all users aggregated together.

Exemplary uses for model 440 include, but are not limited to, classification of events, detection of abnormalities, detection of unexpected events, prediction of events, determination of appropriate interventions, etc.

Those (e.g., doctors, caregivers, etc.) with permission to access the user's data 435 and/or models 440 may do so via private access terminal 455 via communication (e.g. a request and an answer to the request) between private access terminal 455 and server 420 via communication network/remote server 410B. In some embodiments, permission to use private access terminal may be limited to those granted permission by the users and/or healthcare providers associated with the data of a particular user stored in database 415.

A user of public access terminal 445 may not have permission to view personally identifiable information associated with one or more users and may therefore only access anonymous and/or aggregated user data 425 and/or models 440 as may be stored in database 430 via communication between public access terminal 445 and server 420 which may be facilitated by public access terminal 455 and server 420 via public access terminal 455 and server 420 via communication network/remote server 410B.

System 400 may be used to aggregate data from a plurality users and/or communication devices 310 and this data may be used to, for example, use machine learning, or other processes, to identify commonalities and/or trends within the data that may be used to diagnose and/or monitor the lung condition and/or health of users. Additionally, or alternatively aggregated data from a plurality of users may be used to learn trends in trapped air volumes, or other breathing issues, that may be used to predict adverse events or other complications for users. Additionally, or alternatively aggregated data from a plurality of users may be used to generate and/or use a large-scale transactional model that may be used in relation to, for example, monitoring users diagnosed with COPD for other breathing disorders.

Figure 5:
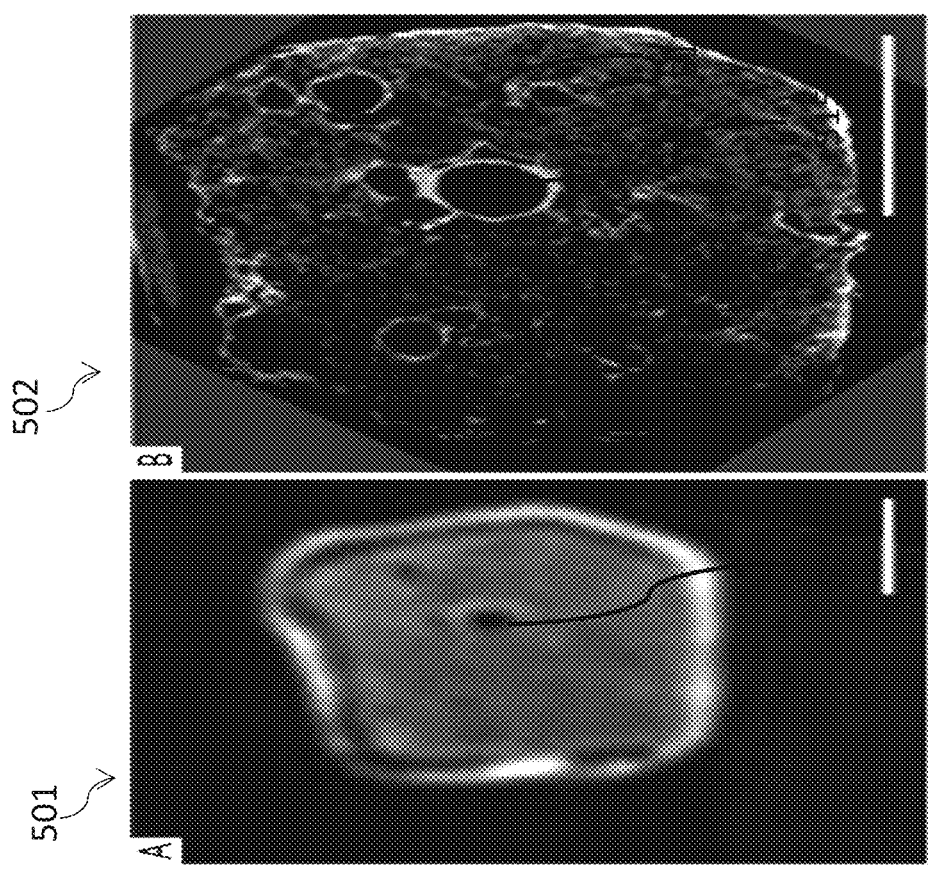
FIG. 5A provides an image of a scanned lung with a small volume of air trapped therein, consistent with some embodiments of the present invention FIG. 5B provides an image of a scanned lung affected with COPD that includes a plurality of pockets, or volumes, of trapped air, consistent with some embodiments of the present invention.

FIG. 5A provides an image 501 of a scanned, relatively healthy lung with a small volume of air trapped therein which is shown in image 501 as a dark spot. FIG. 5B provides an image 502 of a scanned lung affected with COPD that includes a plurality of pockets, or volumes, of trapped air, which are shown in image 502 as a plurality of dark spots.

Figure 6:
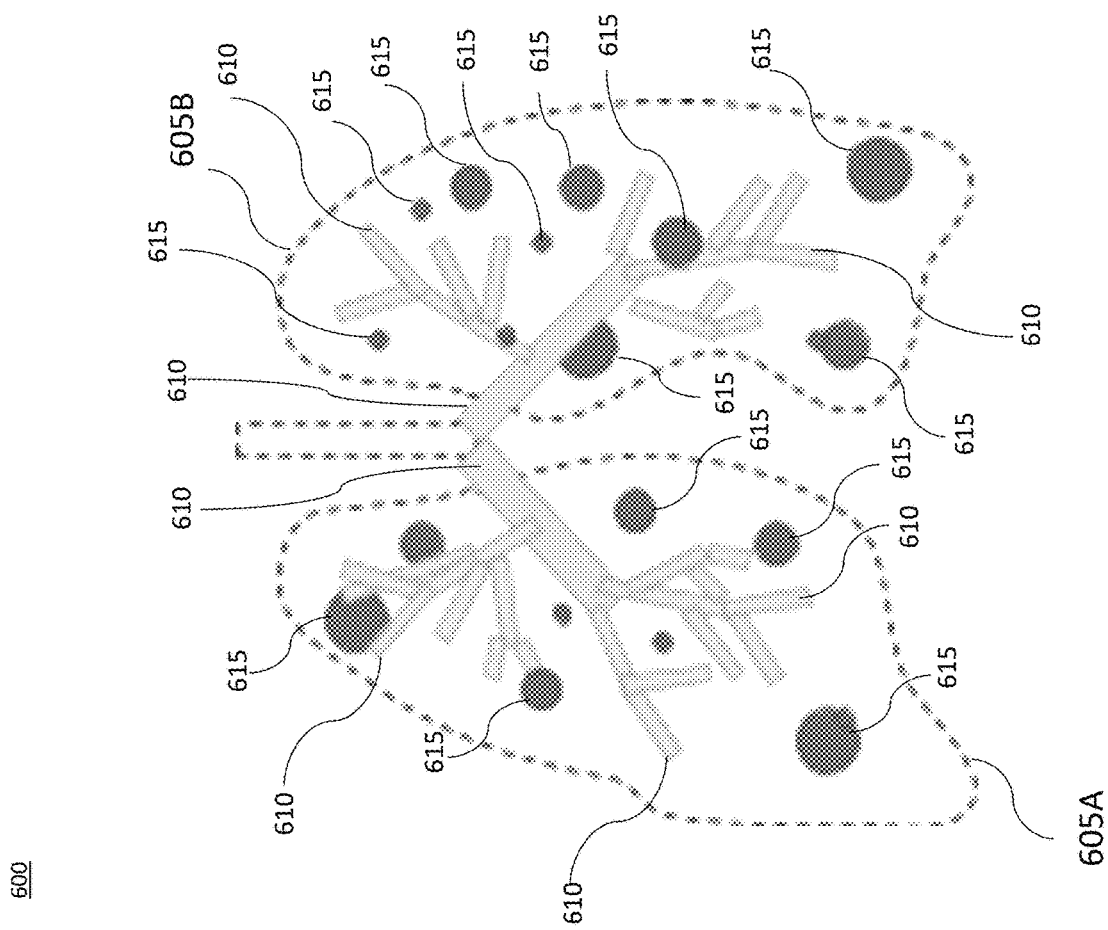
FIG. 6 provides an image of an exemplary manner in which a user's left lung and right lung may be modeled or approximated, consistent with some embodiments of the present invention.

FIG. 6 provides an image 600 of an exemplary manner in which a user's left lung 605A and right lung 605B may be modeled or approximated with tubes 610 that have one or two open ends that may represent bronchial airways and circles 615 that may represent spherical, or approximately spherical, volumes of trapped air. The model shown in FIG. 6 may be based on, for example, an image like image 501 and/or 502 that shows pockets of trapped air and/or received acoustic signals.

Exemplary data that may be used to build a model of a user's lungs with approximations of the bronchial tubes and pockets of trapped air is provided in Tables 1 and 2 below. In some instances, this data may be used to establish one or more relative measurements for trapped air volumes and/or a set of measurements/determinations that may be unique (or specific) to a particular user depending on, for example, the user's lung characteristics (e.g., airway size, lung size, and trapped air volumes), which, in some instances, may serve as a baseline from which subsequent measurements may be compared. On some occasions, these measurements and/or determinations may be considered a score or lung health score.

Lungs airways vary in length and diameter from major to minor and generally reduce in size on each ramification as shown in Table 2. The airway shape is approximated as a tube closed in one or both ends. Although airways are connected, the change in diameter changes the impedance of sound/acoustic energy and acts as if the tube were closed on that end for many frequencies. The expected frequencies may be determined for tubes with one or two closed ends to get a range estimate of the diameter. The resonant frequency for each airway can be computed using Equation 1:

$$f = \frac{v}{4(L + 0.4d)} \quad \text{Equation 1}$$

Where v is the speed of sound, L the length of the tube and d the diameter of the tube for a tube closed in one end (for a tube closed in 2 ends, d=0). The speed of sound in air at 20° C. is 343 meters/second. The speed of sound on air at 37° C. (the temperature of a human being through which the sound is traveling) can be estimated with Equation 2:

$$v = 331.4 + 0.6T_c \quad \text{Equation 2}$$

Where Tc is the temperature in degrees Celsius. The speed of sound on air at 37° C. is 353.6 m/s In one example, a resonant frequency the right (fr) and left (fl) main bronchus with two closed ends and one closed end for a left lung and right lung may be determined inputting the following values into Equation 1:

v=353.6 m/s

Right lung L=0.025 m

Left lung L=0.05 m

Right lung d=0.014 m

Left lung d=0.010 m

TABLE 1

Estimating expected resonant frequencies for airways in the left and right bronchus

| Closed both ends | Closed 1 end |
|---|---|
| $f_r = \dfrac{353.6}{4(0.025)} = 3536$ Hz | $f_r = \dfrac{353.6}{4(0.025 + 0.4 \times 0.014)} = 2888.9$ Hz |
| $f_l = \dfrac{353.6}{4(0.050)} = 1768$ Hz | $f_l = \dfrac{353.6}{4(0.050 + 0.4 \times 0.010)} = 1637.0$ Hz |

Following a similar process, all the other airways can be computed, as shown in table 2.

TABLE 2

Estimated resonances for airways

| Airway Name | Length (mm) | Diameter (mm) | Resonant frequency of tube with 2 closed ends | Resonant frequency of tube with 1 closed end |
|---|---|---|---|---|
| Right main bronchus | 25 | 14 | 3536 Hz | 2888.9 Hz |
| Left main bronchus | 50 | 10 | 1768 Hz | 1637.0 Hz |
| Lobar bronchi | 20 (estimated) | 10 | 4420 Hz | 3683.3 Hz |
| Segmental bronchi | 10 to 15 | 4.5 to 13 | 5893-8840 Hz | 5261.9-8403.0 Hz |
| Subsegmental bronchi | 3 to 10 | 1 to 6 | 8840-29466 Hz | 7129-26000 Hz |

The values of Table 2 may model a lung's (or lung airway's) interaction with sound so that, for example, a range of expected resonant sound frequencies for a lung airway in the form of a pipe may be approximated. A closed pipe may be a model for a big pipe that fits into a smaller one (like airways narrowing down), from the point of view of the air, the narrowing down behaves as if there was a wall there. The model of Table 2 may assist with selecting an appropriate range of frequencies to be injected into the lung and/or narrow down analysis of the detected sound by selectively looking at frequencies that are most likely to correspond with a particular user's lung anatomy/airway size.

Trapped air may be understood as the air remaining in the lungs after exhalation and determining how much air is trapped in a user's lungs may be useful for COPD prognosis. The size and distribution of trapped air volumes may in the range of, for example, 1 to 5 mm of diameter and the volume may be modeled and/or approximated as spheres with a small circular opening (vented sphere). At times, the content of these volumes/spheres of trapped air may be air depleted of oxygen with a higher amount carbon dioxide than ambient air. The speed of sound in carbon dioxide is 259 m/s (lower than in air). In one example, a speed of sound between the speed in air and carbon dioxide (e.g., 300 m/s) may be used.

The resonant frequency of a vented sphere is given by Equation 3:

$$f = \frac{v}{\pi}\sqrt{\frac{3d}{8(0.85)D^3}} \qquad \text{Equation 3}$$

Where:

v=the speed of sound in the gas

D=diameter of the sphere, and d=the diameter of the opening

The resonant frequencies of volumes of trapped air of differing exemplary sizes have been calculated using Equation 3 and v=300 m/s and are provided in Table 3 below.

TABLE 3

Estimated resonances for trapped air volumes

| Diameter Sphere (mm) | Diameter opening (mm) | Resonant frequency (Hz) |
|---|---|---|
| 10 | 2.5 | 25370 Hz |
| 20 | 5.0 | 12685 Hz |
| 30 | 7.5 | 8457 Hz |
| 40 | 10 | 6342 Hz |
| 50 | 12.5 | 5074 Hz |

The values of Table 3 may be used to develop a model of trapped air's interaction with sound by approximating the volume of trapped air as a spherical air bubble so that a baseline of resonant frequencies that may be expected for a model air volume of trapped air may be determined.

The simplified lung model of Tables 1-3 may indicate acoustic resonances in the frequency range of 1.6 KHz to 30 KHz, thus providing an indication of a range of frequencies that are most likely to produce resonance within the lung, which correspond to frequencies of interest to project into the lungs or otherwise track in order to determine a user's lung resonance. For each individual lung, or set of lungs, the specific resonances measured will be different, based on their actual lung characteristics including, but not limited to, airway size, trapped air volumes, etc. Each person's measured resonances may be referred to as a lung resonance signature (LRS). Each user's LRS may change over time and tracking these changes may assist with the monitoring or otherwise diagnosing lung health and/or disease progression. In some embodiments, instantaneous, or rapid, changes in LRS help establish respiratory cycle.

The values of Tables 2 and/or 3 may be used to model a range of expected resonant frequencies in healthy human lungs, and/or lungs of people with COPD. The values may be used to determine a set of frequencies that are resonant for the lungs of particular users. Because the lung anatomy (e.g., bronchial tube shape, length, diameter, etc.) are highly specific to an individual, resonant frequencies for each individual user's lungs are expected to vary from user to user. Once a user's baseline of resonant frequencies is established, it may be used to track changes thereto over time. These changes may indicate a change in lung condition, a development of a pathology, and/or a worsening of a condition that may be indicative of an impending severe event (that may require hospitalization).

In some embodiments, resonant frequencies for a plurality of users may be determined and aggregated together to find patterns of resonances of lungs and/or trapped air across the plurality of users. This may be used for, monitoring, and/or prognostic purposes in order to, for example, diagnosis COPD and/or determine a severity of a COPD condition for a user.

Figure 7:
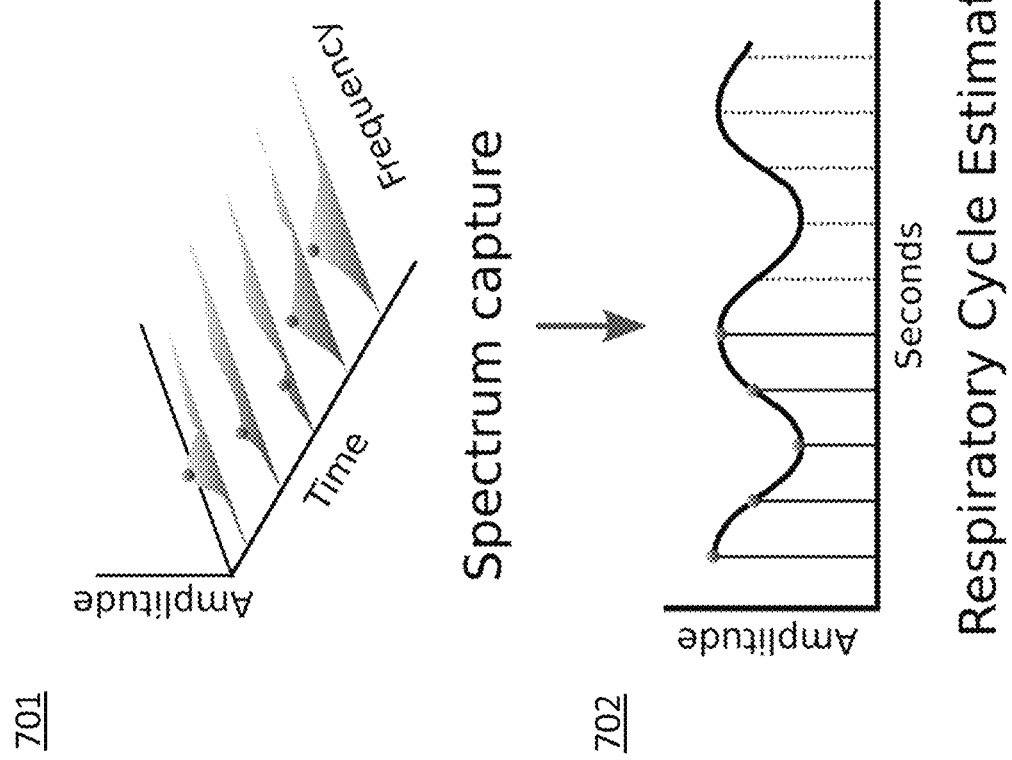
FIG. 7A shows a spectrum capture three-dimensional graph of sound that has passed through a user's lungs and has been received by a receiver, consistent with some embodiments of the present invention.
FIG. 7B shows a graph of respiratory cycle estimation, consistent with some embodiments of the present invention.

FIG. 7A shows a spectrum capture three-dimensional graph 701 of sound that has passed through a user's lungs and has been received by a receiver via an active auscultation system like active auscultation system 100, 200, and/or 201 with amplitude on the Z-axis, time on the X-axis, and frequency on the Y-axis. The spectrum capture shows the peak amplitude of a resonant region for different time periods as a dot. FIG. 7B also shows a graph of respiratory cycle estimation 702 which plots the maximum amplitudes from graph 701 as a function of time in seconds.

Figure 8:
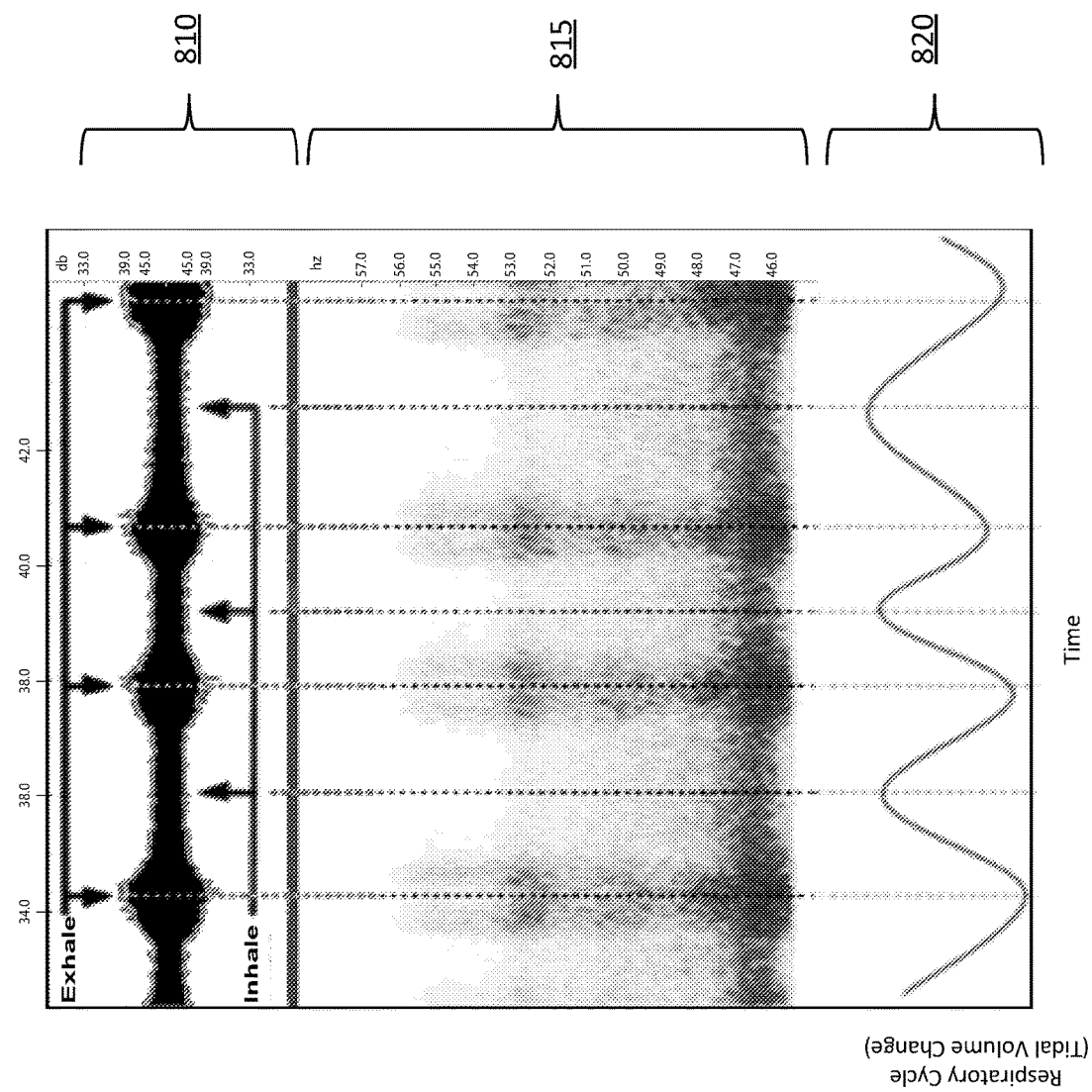
FIG. 8 provides a series of graphs of some exemplary sound that may be continuously emitted over time by an emitter into a user's lungs and received via an active auscultation system, consistent with some embodiments of the present invention.

FIG. 8 provides a series of graphs 800 of some exemplary sound that may be continuously emitted over time by an emitter like emitter 110 that has been projected into a user's lungs and received via an active auscultation system like active auscultation system 100, 200, and/or 201 by a receiver like receiver 115. The raw received sound is shown on the first graph 810 as a waveform that varies in intensity/power measured in decibels (dB) with time in seconds on the X-axis and intensity or power shown on the Y axis in dB. As may be seen in graph 810, the intensity of the received sound decreases with user's inhalation and increases with the user's exhalation. A second graph 815 of FIG. 8 shows frequency spectrum changes in Hz that change over time and correspond, in time, to the values of first graph 810. FIG. 8 also shows a third graph 820 that provides a corresponding estimated respiratory cycle, or total change in air volume, for the user that corresponds in time with the values of first and second graphs 810 and 815.

Figure 9:
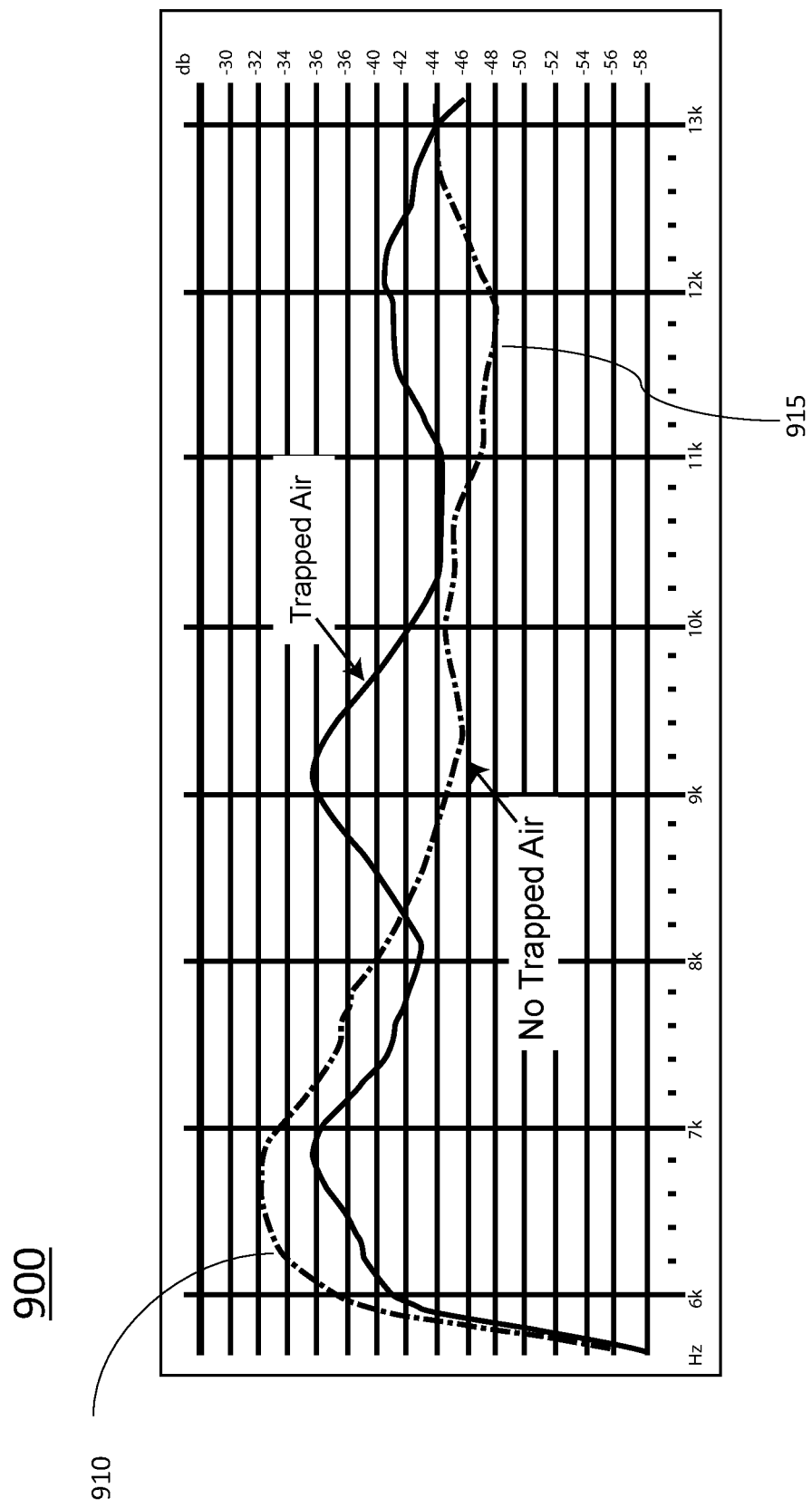
FIG. 9 provides a graph of exemplary lung resonance signature (LRS) data, consistent with some embodiments of the present invention.

FIG. 9 provides a graph 900 of exemplary lung resonance signature (LRS) data for a user showing frequency in Hz as a function of intensity or power in dB. Graph 900 provides a first line 910 that shows a range of frequencies and intensities for a lung with trapped air and a second line 915 that shows a range of frequencies and intensities for a lung without trapped air.

The sound detected by the one or more detectors in communication with a user may be used in any number of ways to deduce a physiological condition of a patient or user. For example, the detected sound may be analyzed to determine a spectral shape of the sound, which may be understood as a relative or absolute relationship between a range of detected frequencies. In addition to spectral shape, a spectral tilt might be determined by analyzing the received sound to determine if the energy and/or intensity of detected frequencies increases and/or decreases with the frequency and/or if any peaks or valleys in intensity/energy of the detected sound occur for particular frequencies or ranges of frequencies. In some instances, the spectral shape of the detected sound may include information regarding how many peaks and/or valleys in intensity/power of detected sound occur across a frequency range, and any other feature such as slope of the shape, region of maximum energy, region of minimum energy.

The spectral shape of detected sound may be measured and/or determined instantaneously, periodically, and/or as-needed and, in some instances, multiple spectral shape measurements/determinations may be made over time so that a user's response to the input sound may be monitored to, for example, determine changes and/or a rate of change. This may be helpful to track rapid or slow improvements or declines in the user's condition.

In some cases, detected sound may also be analyzed to determine a spectral centroid (also referred to as a "center of mass") for a frequency spectrum of detected/received sound/acoustic energy. In some instances, a spectral centroid may be calculated as a weighted mean of the frequencies present in the detected/received sound. In some cases, this calculation may be performed using a Fourier transform with the magnitudes of a particular frequency shown as weights in the Equation 4 below:

$$\text{Centroid} = \frac{\sum_{n=0}^{N-1} f(n)x(n)}{\sum_{n=0}^{N-1} x(n)} \qquad \text{Equation 4}$$

where:
  x(n)=the weighted frequency value, or magnitude, of bin number n; and
  f(n)=the center frequency of that bin.

This spectral centroid may be tracked over time to monitor, for example, a range of frequencies detected and/or received by an active auscultation system like active auscultation system 100, 200, and/or 201.

Additionally, or alternatively, harmonics and/or harmonic changes of the detected sound may be analyzed to determine a spectral signature of the detected sound. This analysis may reveal portions of the detected signal of higher and/or lower power/intensity (i.e., peaks and/or valleys in the intensity or power of the detected sound, respectively) and/or relationships of different frequencies within the detected sound. Sometimes these relationship different frequencies may be simple and present regular patterns (e.g., harmonics). Additionally, or alternatively, spacing between bulges, changes in spacing, relative amplitude, etc. of detected sound/acoustic energy may be analyzed and monitored over time to determine changes or patterns, which may be of diagnostic interest.

For embodiments specific to COPD, the present invention may be used to monitor lung function and health of a user by measuring, or otherwise assessing, a volume of air remaining in the lungs of the user after completely exhaling (i.e., a volume of trapped air), which can be in indicator of COPD prognosis and lung health for users diagnosed with COPD. In one instance, a acoustic resonance of a user's lung, or lungs, may be measured and/or determined and/or modeled based on one or more parameters as described herein.

In some embodiments, a pair of emitters and receivers configured for use with a user's right and left lung (i.e., one emitter and one receiver per lung). This embodiment may employ stereo sound card playback and capture. Signals received by the receiver may be analyzed to, for example, detect and/or characterize cross-channel leakage (e.g., sound projected in the left lung is received by the receiver for the right lung) by measuring the amount and frequency signature of stimuli from one channel to the other. It is contemplated that "orthogonal" stimuli may be used for both channels (i.e., the sound projected into both lungs). This may minimize cross-interference (e.g. use varied pseudorandom sequences, or time divisions to measure each channel at a different time) between the channels.

In some cases, when a pair of emitters and receivers are used, stimuli may be provided to a first emitter for the left lung and the receiver for the second lung may be used to determine how much cross-channel leakage is detected. This process may be reversed to see if there is cross-channel leakage from the sound projected into the second lung at the receiver for the first lung. If cross-channel leakage is detected, an orthogonal noise-like signal may be created and used as stimuli for one or both of the emitters. Cross-channel leakage may then be measured by providing the signal to both lungs and measuring detected sound with both detectors simultaneously. The knowledge of pseudorandom sequence used to generate the sound may be used to infer the contribution from each channel received at a detector. This may be used to remove an estimated leakage contribution from a detected signal.

Figure 10:
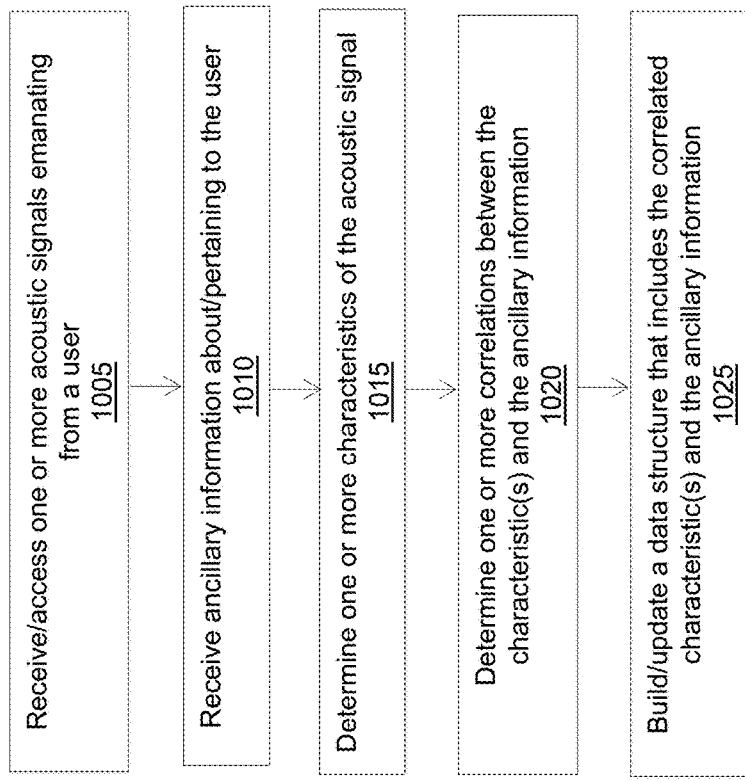
FIG. 10 provides a flowchart depicting a process, consistent with some embodiments of the present invention.

FIG. 10 provides a flowchart illustrating a process 1000 for determining a correlation between a characteristic of an acoustic signal received by, for example, an active auscultation system like active auscultation systems 100, 200 and/or 201 and ancillary information for a user from whom the acoustic signal has been received. Process 1000 may be executed by any system and/or system component disclosed herein.

Initially, in step 1005, one or more acoustic signals emanating from a user may be received by, for example, a processor like processor/memory 160 and/or a server like server 420 from, for example, a receiver like receiver 115 and/or an active auscultation system like active auscultation 100, 200, and/or 201. Ancillary information may then be received in step 1010. Ancillary information like the ancillary information described above may be received in step 1010. Exemplary ancillary information includes, but is not limited to, information received from the user (e.g., medical information, onset of a medical complication or emergency, mental health status information, etc.) via, for example, interaction with a communication device like communication device 310 and/or may be received directly from the communication device. Ancillary information received directly from the communication device may include geographic information, altitude, local weather information, local air quality information, and the like. Additionally, or alternatively, ancillary information may include information captured by a software application running on the communication device. Exemplary software applications may gather information pertaining to, for example, a level of activity for the user, and a heartrate of the user, a blood oxygen saturation level of the user.

In step 1015, one or more characteristics of the acoustic signal may be determined and/or received. The characteristics determined may include any of the characteristics described herein. In step 1020, one or more correlations between a characteristic of the acoustic signal and the characteristic(s) may be determined. Then, in step 1025, a data structure like database 415 and/or 430 may be built and/or updated using the received acoustic signal, ancillary information, and correlations therebetween. In some embodiments, the data structure of step 1025 may be made via a process similar to the process for developing model 440.

Figure 11:
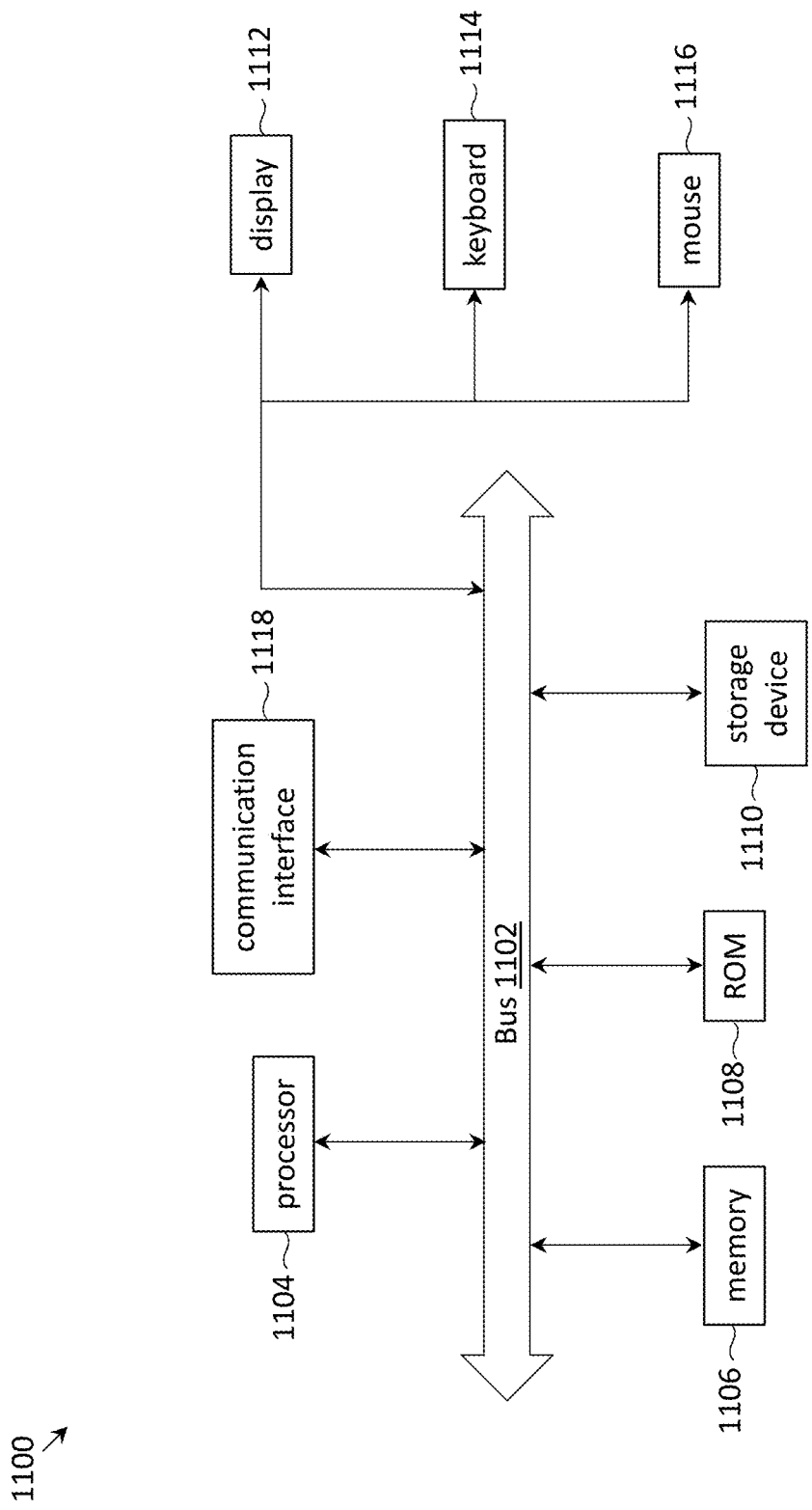
FIG. 11 depicts components of a computer system in which computer readable instructions instantiating the methods of the present invention may be stored and executed, consistent with some embodiments of the present invention.

As is apparent from the foregoing discussion, aspects of the present invention involve the use of various computer systems and computer readable storage media having computer-readable instructions stored thereon. FIG. 11 provides an example of a system 1100 that may be representative of any computing system that may be used to instantiate a respiratory disease model and/or perform a process, or a portion of a process described herein. Examples of system 1100 may include a smartphone, a desktop, a laptop, a mainframe computer, an embedded system, etc. Note, not all of the various computer systems have all of the features of system 1100. For example, certain ones of the computer systems discussed above may not include a display inasmuch as the display function may be provided by a client computer communicatively coupled to the computer system or a display function may be unnecessary. Such details are not critical to the present invention. System 1100, or portions thereof, may be, for example, an active auscultation system like active auscultation systems 110, 200 and/or 201 system like a communication device like communication device 311, a server like server 420, and/or a computer terminal like private access terminal 455 and public access terminal 445 and/or components thereof.

System 1100 includes a bus 1102 or other communication mechanism for communicating information and a processor 1104 coupled with the bus 1102 for processing information. Computer system 1100 also includes a main memory 1106, such as a random-access memory (RAM) or other dynamic storage device, coupled to the bus 1102 for storing information and instructions to be executed by processor 1104. Main memory 1106 also may be used for storing temporary variables or other intermediate information during execution of instructions by processor 1104. Computer system 1100 further includes a read only memory (ROM) 1108 or other static storage device coupled to the bus 1102 for storing static information and instructions for the processor 1104. A storage device 1111, for example a hard disk, flash memory-based storage medium, or other storage medium from which processor 1104 can read, is provided and coupled to the bus 1102 for storing information and instructions (e.g., operating systems, applications programs and the like).

Computer system 1100 may be coupled via the bus 1102 to a display 1112, such as a flat panel display, for displaying information to a computer user. An input device 1111, such as a keyboard including alphanumeric and other keys, may be coupled to the bus 1102 for communicating information and command selections to the processor 1104. Another type of user input device is cursor control device 1116, such as a mouse, a trackpad, or similar input device for communicating direction information and command selections to processor 1104 and for controlling cursor movement on the display 1112. Other user interface devices, such as microphones, speakers, etc. are not shown in detail but may be involved with the receipt of user input and/or presentation of output.

The processes referred to herein may be implemented by processor 1104 executing appropriate sequences of computer-readable instructions contained in main memory 1106. Such instructions may be read into main memory 1106 from another computer-readable medium, such as storage device 1111, and execution of the sequences of instructions contained in the main memory 1106 causes the processor 1104 to perform the associated actions. In alternative embodiments, hard-wired circuitry or firmware-controlled processing units may be used in place of or in combination with processor 1104 and its associated computer software instructions to implement the invention. The computer-readable instructions may be rendered in any computer language.

In general, all of the above process descriptions are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 1100 or similar electronic computing device, that manipulates and transforms data represented as physical (electronic) quantities within its registers and memories into other data similarly represented as physical quantities within its memories or registers or other such information storage, transmission or display devices.

Computer system 1100 also includes a communication interface 1118 coupled to the bus 1102. Communication interface 1118 may provide a two-way data communication channel with a computer network, which provides connectivity to and among the various computer systems discussed above. For example, communication interface 1118 may be a local area network (LAN) card to provide a data communication connection to a compatible LAN, which itself is communicatively coupled to the Internet through one or more Internet service provider networks. The precise details of such communication paths are not critical to the present invention. What is important is that computer system 1100 can send and receive messages and data through the communication interface 1118 and in that way communicate with hosts accessible via the Internet. It is noted that the components of system 1100 may be located in a single device or located in a plurality of physically and/or geographically distributed devices.

I claim:

1. A method of performing active auscultation comprising:
   providing, by a processor in communication with an emitter, a set of signal stimuli to the emitter so that the emitter produces a set of acoustic energy directed into a user's body toward a user's lung;
   receiving, by the processor, an acoustic energy response from a receiver communicatively coupled to the processor, the acoustic energy response being responsive to the set of acoustic energy directed into the user's body;
   determining, by the processor, a resonant frequency included within the acoustic energy response; and
   determining, by the processor, a volume of trapped air present in the user's lung using the resonant frequency, the volume of trapped air being air that is trapped within discrete pockets of lung tissue of the user's lung following the user's exhalation of air from the user's lung.

2. The method of claim 1, wherein the set of signal stimuli is a first set of signal stimuli, the set of acoustic energy directed into the user's lung is a first set of acoustic energy, the acoustic energy response is a first acoustic energy response, and the volume of trapped air present in the user's lung is a first volume of trapped air present in the user's lung, the method further comprising:
   providing, by the processor, a second set of signal stimuli to the emitter so that the emitter produces a second set of acoustic energy directed into a user's body toward a user's lung;
   receiving, by the processor, a second acoustic energy response from the receiver, the second acoustic energy response being responsive to the second set of acoustic energy directed into the user's body;
   determining, by the processor, a resonant frequency included within the second energy response;
   determining, by the processor, a second volume of trapped air present in the user's lung responsively to the resonant frequency included within the second acoustic energy response, the second volume of trapped air being air that is trapped within discrete pockets of lung tissue of the user's lung following the user's exhalation of air from the user's lung;
   comparing, by the processor, the first volume of trapped air and the second volume of trapped air present in the user's lung; and
   providing, by the processor, an indication of the comparing to an operator.

3. The method of claim 2, wherein the discrete pockets of lung tissue trapping the first volume of trapped air correspond to the discrete pockets of lung tissue trapping the second volume of trapped air.

4. The method of claim 2, wherein one or more of the discrete pockets of lung tissue trapping the first volume of trapped air are different from one or more of the discrete pockets of lung tissue trapping the second volume of trapped air.

5. The method of claim 1, further comprising:
   comparing, by the processor, the volume of trapped air present in the user's lung to a predetermined value.

6. The method of claim 1, further comprising: generating, by the processor, an adjusted set of signal stimuli by adjusting at least one of a duration of the set of signal stimuli, an intensity of the set of signal stimuli, and frequencies included in the set of signal stimuli responsively to the resonant frequency included within the acoustic energy response signal determined characteristics of the acoustic signal.

7. The method of claim 1, wherein the set of signal stimuli causes the emitter to emit acoustic energy that comprises a plurality of frequencies between 2,000 Hz and 30,000 Hz.

8. The method of claim 1, wherein the set of acoustic energy is directed toward the user's lung for a time period lasting between 0.1 seconds and 2 seconds.

9. The method of claim 1, wherein the set of acoustic enemy includes a plurality of pseudo-randomly selected frequencies.

10. The method of claim 1, wherein the determining of a resonant frequency included within the acoustic energy response includes determining a plurality of resonant frequencies included within the acoustic energy response.

11. A method comprising: receiving, by a processor, a detected acoustic signal from a receiver, the detected acoustic signal corresponding to an acoustic signal pulse directed toward a user's lung and responsively emanating from the user's lung;
   analyzing, by the processor, the received detected acoustic signal to determine a resonant frequency for the user's lung; and
   determining, by the processor, a volume of trapped air present in the user's lung responsively to the resonant frequency, the volume of trapped air being air that is trapped within discrete pockets of lung tissue of the user's lung following the user's exhalation of air from the user's lung.

12. The method of claim 11, further comprising: comparing, by the processor, the resonant frequency of the user's lung to a predetermined value.

13. The method of claim 11, furthering comprising:
generating, by the processor, an adjusted signal pulse by adjusting at least one of a duration, an intensity, and frequencies included in the acoustic signal pulse responsively to the resonant frequency included within the detected acoustic signal.

14. The method of claim 11, wherein the acoustic signal pulse includes frequencies within a range of 2,000 Hz and 30,000 Hz.

15. The method of claim 11, wherein the acoustic signal pulse includes a plurality of pseudo-randomly selected frequencies.

16. The method of claim 11, wherein the determining of a resonant frequency included within the acoustic energy response includes determining a plurality of resonant frequencies included within the acoustic energy response.

17. The method of claim 11, wherein the acoustic signal pulse lasts between 0.1 seconds and 2 seconds.

18. A method for performing active auscultation comprising:
providing, by a processor in communication with an emitter, signal stimuli to the emitter so that the emitter produces acoustic energy that includes a plurality of pseudo-randomly selected frequencies, the acoustic energy being directed towards a lung of a user;
receiving, by the processor, via a receiver in communication with the processor, an acoustic energy response emanating from the user that corresponds to the acoustic energy directed towards to the user's lung; organ; and
analyzing, by the processor, the acoustic energy response to determine a resonant frequency for the user's lung;
determining, by the processor, a volume of trapped air present in the user's lung using to the resonant frequency, the volume of trapped air being air that is trapped within discrete pockets of lung tissue of the user's lung following the user's exhalation of air from the user's lung.

19. The method of claim 18, wherein the signal stimuli causes the emitter to produce a set of discrete frequencies.

20. The method of claim 19, wherein the signal stimuli cause the emitter to produce acoustic energy that cycles through the set of discrete frequencies over a predetermined period of time.

21. The method of claim 18, wherein signal stimuli cause the emitter to produce a burst of acoustic energy that includes the plurality of pseudo-randomly selected frequencies.

22. The method of claim 18, further comprising: receiving, by the processor, information pertaining to the user; and correlating, by the processor, the information with the resonant frequency of the user's lung.

23. The method of claim 22, wherein the information pertains to one or more of a physiological characteristic of the user, a diagnosis of the user, a size of the lung, a shape of the lung, a type of fluid in the lung, a type of gas in the lung, a location of the emitter, a location of the receiver, a level of ambient noise proximate to the user, and an orientation of the user.

24. The method of claim 18, wherein signal stimuli cause the emitter to produce an acoustic signal with one or more of a predetermined frequency response and a predetermined frequency bin.

25. The method of claim 18, wherein the determining of a resonant frequency included within the acoustic energy response includes determining a plurality of resonant frequencies included within the acoustic energy response.

* * * * *